United States Patent
Tsukamoto et al.

(10) Patent No.: US 6,774,266 B2
(45) Date of Patent: Aug. 10, 2004

(54) PROCESS FOR PRODUCING 1,1,1-TRIFLUOROACETONE

(75) Inventors: Masanori Tsukamoto, Saitama (JP); Takashi Sakaya, Yamaguchi (JP); Takayuki Nishimiya, Saitama (JP); Junji Negishi, Saitama (JP)

(73) Assignee: Central Glass Company, Limited, Yamaguchi (JP)

( * ) Notice: Subject to any disclaimer, the term of this patent is extended or adjusted under 35 U.S.C. 154(b) by 0 days.

(21) Appl. No.: 10/299,996

(22) Filed: Nov. 20, 2002

(65) Prior Publication Data

US 2003/0114713 A1 Jun. 19, 2003

(30) Foreign Application Priority Data

Nov. 20, 2001 (JP) ........................................ 2001-355054

(51) Int. Cl.[7] .............................................. C07C 45/00
(52) U.S. Cl. ........................ 568/392; 568/394; 568/411
(58) Field of Search ................................. 568/392, 394, 568/411

(56) References Cited

U.S. PATENT DOCUMENTS 5,905,174 A  5/1999  Kanai et al. ................. 568/411
6,262,312 B1  7/2001  Goto ........................... 568/394
6,340,776 B2  1/2002  Goto et al. .................. 568/394

FOREIGN PATENT DOCUMENTS

JP  2000-336057 A  12/2000

*Primary Examiner*—S. Kumar
*Assistant Examiner*—Sikarl A. Witherspoon
(74) *Attorney, Agent, or Firm*—Crowell & Moring LLP

(57) ABSTRACT

A process for producing 1,1,1-trifluoroacetone includes the step of conducting in a gas phase a hydrogenolysis of a tetrafluoroacetone, which is represented by the general formula [1], by a hydrogen gas in the presence of a catalyst containing a transition metal,

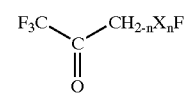

[1]

where X represents a chlorine, bromine or iodine, and n represents an integer from 0 to 2.

14 Claims, No Drawings

PROCESS FOR PRODUCING 1,1,1-TRIFLUOROACETONE

BACKGROUND OF THE INVENTION

The present invention relates to a process for producing 1,1,1-trifluoroacetone that is useful as an intermediate of pharmaceuticals and agricultural chemicals, or as a reagent for introducing fluorine-containing groups.

U.S. Pat. No. 6,262,312 B1, corresponding to Japanese Patent Unexamined Publication 2000-336057A, discloses a process for industrially producing 1,1,1-trifluoroacetone by reacting in a liquid phase 3-halogenated-1,1,1-trifluoroacetone (hereinafter "halogenated trifluoroacetone"), which is represented by the following general formula [2], with metallic zinc in a solvent of a proton donor.

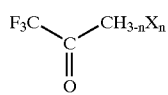

[2]

where X is a chlorine, bromine or iodine; and n is an integer of 1–3.

U.S. Pat. No. 6,340,776 B2, corresponding to Japanese Patent Application Serial No. 2000-309649, discloses a process for producing 1,1,1-trifluoroacetone by conducing in a gas phase a hydrogenolysis of the halogenated trifluoroacetone represented by the general formula [2], using a metallic catalyst.

SUMMARY OF THE INVENTION

It is an object of the present invention to provide a process for efficiently producing 1,1,1-trifluoroacetone using as a raw material a tetrafluoroacetone of the general formula [1] containing four fluorine atoms,

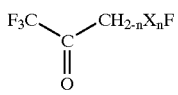

[1]

where X is a chlorine, bromine or iodine, and n is an integer of 0–2.

Since carbon-fluorine bond is stronger than each of carbon-chlorine bond, carbon-bromine bond and carbon-iodine bond, it is more difficult to replace the fluorine atom of $CH_{2-n}X_nF$ group of the tetrafluoroacetone with hydrogen, as compared with the halogen atom of $CH_{3-n}X_n$ of the trifluoroacetone. If the reduction conditions are made too severe in order to increase the reactivity, the carbonyl group and the trifluoromethyl group are subjected to hydrogenation.

It is therefore a more specific object of the present invention to provide a process for producing 1,1,1-trifluoroacetone from the tetrafluoroacetone in a manner to efficiently convert $CH_{2-n}X_nF$ group of the tetrafluoroacetone into methyl group and to substantially suppress the hydrogenation of the carbonyl group and the trifluoromethyl group of the tetrafluoroacetone.

According to the present invention, there is provided a process for producing 1,1,1-trifluoroacetone. This process comprises conducting in a gas phase a hydrogenolysis of the tetrafluoroacetone, which is represented by the general formula [1], by a hydrogen gas in the presence of a catalyst comprising a transition metal (e.g., ruthenium, palladium, platinum, iridium, rhodium, nickel, and a mixture of these).

According to the present invention, it is unexpectedly possible to efficiently achieve selective hydrogenation of $CH_{2-n}X_nF$ group of the tetrafluoroacetone into methyl group and thereby to easily and efficiently obtain 1,1,1-trifluoroacetone with a remarkably high yield.

DESCRIPTION OF THE PREFERRED EMBODIMENTS

The hydrogenolysis of the present invention can be conducted by a gas phase reaction between the tetrafluoroacetone (gas) of the general formula [1] and hydrogen gas using a reactor for flow method.

The tetrafluoroacetone can be selected from 1,1,1,3-tetrafluoroacetone, 3-chloro-1,1,1,3-tetrafluoroacetone, 3,3-dichloro-1,1,1,3-tetrafluoroacetone, 3-bromo-1,1,1,3-tetrafluoroacetone, 3,3-dibromo-1,1,1,3-tetrafluoroacetone, 3-iodo-1,1,1,3-tetrafluoroacetone, 3,3-diiodo-1,1,1,3-tetrafluoroacetone, 3-bromo-3-chloro-1,1,1,3-tetrafluoroacetone, 3-bromo-3-iodo-1,1,1,3-tetrafluoroacetone, 3-chloro-3-iodo-1,1,1,3-tetrafluoroacetone, and mixtures of these.

These compounds can be synthesized, for example, based on the method of Example 1 of U.S. Pat. No. 5,905,174, of which disclosure is incorporated herein by reference. In fact, it is disclosed therein that 1-chloro-1,3,3,3-tetrafluoroacetone (corresponding to the tetrafluoroacetone) can be obtained together with 3,3-dichloro-1,1,1-trifluoroacetone (corresponding to the halogenated trifluoroacetone of the general formula [2]) by fluorinating pentachloroacetone (a pentahalogenoacetone). Furthermore, it is possible to isolate 1-chloro-1,3,3,3-tetrafluoroacetone by a subsequent purification.

In the hydrogenolysis of the present invention, the halogenated trifluoroacetone of the general formula [2] may be coexistent with the tetrafluoroacetone. When a mixture of these compounds is subjected to a hydrogenolysis of the present invention, each of these compounds is converted into 1,1,1-trifluoroacetone, thereby obtaining a reaction product containing 1,1,1-trifluoroacetone as a main component.

It is optional in the present invention to use solvent for dissolving the tetrafluoroacetone or a mixture of the tetrafluoroacetone and the halogenated trifluoroacetone or to omit such solvent. The resulting solution is in the form of preferably aqueous solution or alcohol solution, more preferably aqueous solution. In case that alcohol is used as the solvent, it is preferable from the viewpoint of availability to use an alcohol, in which hydroxyl group is bonded to a $C_1$–$C_{20}$ alkyl group. In case that the solution is in the form of aqueous solution or alcohol solution, the tetrafluoroacetone may be a hydrate represented by the formula [3], alcohol addition product represented by the formula [4], gem-diol represented by the formula [5], hemiacetal or acetal. The tetrafluoroacetone may take any of these structures.

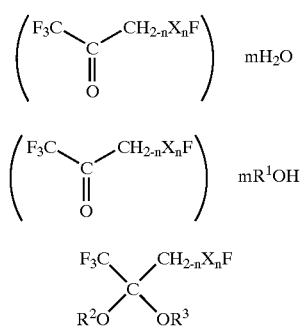

$$\left(\begin{array}{c} F_3C\diagdown_{\underset{\parallel}{C}}\diagup CH_{2-n}X_nF \\ O \end{array}\right) mH_2O \quad [3]$$

$$\left(\begin{array}{c} F_3C\diagdown_{\underset{\parallel}{C}}\diagup CH_{2-n}X_nF \\ O \end{array}\right) mR^1OH \quad [4]$$

$$\begin{array}{c} F_3C\diagdown\;\;\diagup CH_{2-n}X_nF \\ C \\ R^2O\diagup\;\;\diagdown OR^3 \end{array} \quad [5]$$

In the formulas [3]–[5], X and n are defined as in the general formula [1], m is an integer, $R^1$ is an alkyl group, and each of $R^2$ and $R^3$ is independently a hydrogen atom or alkyl group.

In the case of using solvent, its amount is not particularly limited. It is preferably 100 g or less, more preferably 50 g or less, per 100 g of the tetrafluoroacetone or a mixture of the tetrafluoroacetone and the halogenated trifluoroacetone when the latter is coexistent with the former. If it is greater than 100 g, there may arise, for example, a problem of necessity to provide a reaction apparatus of an excessively large size. Therefore, this may not be preferable from the economical viewpoint.

The hydrogenolysis can be conducted by vaporizing the raw material (i.e., the tetrafluoroacetone or a mixture of the tetrafluoroacetone and the halogenated trifluoroacetone) or its solution by a vaporizer, then by introducing the same into a reactor, and then by reacting the same with hydrogen gas in the presence of the catalyst. Upon this, it is optional to make nitrogen gas coexistent with the other reagents in the reaction system in order to adjust the reaction and to suppress the catalyst deterioration.

As stated above, the catalyst used in the hydrogenolysis comprises a transition metal. This transition metal may be a single transition metal or a plurality of transition metals and is preferably ruthenium, palladium, platinum, iridium, rhodium or nickel. Of these, palladium and platinum are particularly preferable. It may be preferable to mix the transition metal with an additional metal (e.g., gold, silver, copper and iron), since the reaction may proceed mildly in some cases. The transition metal is preferably supported on a support such as activated carbon, alumina, silica-alumina, and silica. Of these, activated carbon is preferable. It is particularly preferable to use a catalyst containing an activated carbon supporting thereon palladium or platinum. The way of making the transition metal to be supported on the support is not particularly limited. For example, it is possible to immerse a support in a solution of a transition metal compound or to spray this solution to a support, followed by drying and then reduction with hydrogen gas. The transition metal compound may be in the form of chloride, bromide, fluoride, oxide, nitrate, sulfate or carbonate.

The transition metal (calculated as metallic form) may be in an amount of 0.1–10 g, preferably 0.2–5 g, per 100 g of the support. If it is less than 0.1 g, yield of 1,1,1-trifluoroacetone may become too low. An amount of greater than 5 g may not be preferable from the economical viewpoint.

The reaction temperature may be in a range of 50–300° C., preferably 80–230° C., more preferably 100–170° C. If it is lower than 50° C., the reaction rate may be insufficient. If it is higher than 300° C., hydrogenolysis of the trifluoromethyl group and/or hydrogenation of the carbonyl group may proceed. With this, yield of 1,1,1-trifluoroacetone may be lowered. Furthermore, by-products may interfere with purification.

The molar ratio of hydrogen (hydrogen gas) to the tetrafluoroacetone may be varied depending on the number (n+1) of the halogen atoms of the halogenated fluoromethyl group (—$CH_{2-n}X_nF$). This ratio may be in a range of 1.5–50, preferably 2–10, more preferably 2.5–5. If it is less than 1.5, conversion of the tetrafluoroacetone may not be sufficiently high. Even if it is greater than 50, conversion of the tetrafluoroacetone may not improve further. Furthermore, this is not preferable from the economical viewpoint, due to the necessity of recovering the unreacted hydrogen gas.

It is preferable that the hydrogenolysis is conducted by using a reactor made of a material lined with a lining material selected from tetrafluoroethylene resins, chlorotrifluoroethylene resins, perfluoroalkyl vinyl ether (PFA) resins and carbon, when water (of approximately 100 ppm or higher) exists in the reaction system. When water does not exist in the reaction system (where water content is approximately less than 100 ppm), it is possible to use iron, stainless steel, nickel or Hastelloy (trade name) for the reactor in addition to the above-mentioned lining material. In the hydrogenolysis, hydrogen fluoride is produced as a by-product. Therefore, it is not preferable to use a glass material for the reactor and for other reaction instruments that are to be in contact with the reagents.

The way of conducting the hydrogenolysis is not particularly limited. For example, it can be conducted as follows. At first, a reactor for flow method, which is resistant against the reaction conditions of the hydrogenolysis, is charged with a transition metal supported catalyst. Then, the reactor is heated from outside, and hydrogen gas is allowed to flow through a reaction tube. Alternatively, hydrogen gas and nitrogen gas are allowed to flow simultaneously therethrough. When the reaction tube's inside temperature reaches a predetermined temperature, a mixture of the raw materials containing the tetrafluoroacetone is introduced into a vaporizer for vaporizing the same, followed by mixing with hydrogen gas. The resulting mixture is introduced into the reaction tube. A mixture of gas and/or liquid flowing out of the reaction tube is absorbed into water to cool it down and to collect it in the form of liquid. It is optional to separately introduce the tetrafluoroacetone and hydrogen gas into the reactor.

The resulting 1,1,1-trifluoroacetone can be purified by a conventional purification method used for hydrogenolysis products obtained from fluorinated compounds. For example, a reaction product containing 1,1,1-trifluoroacetone (in the form of liquid or gas), which has flowed out of the reactor together with hydrogen chloride and hydrogen fluoride, is cooled down. After that, hydrogen fluoride is removed from the reaction product by neutralization through a treatment with calcium chloride, calcium hydroxide or calcium carbonate. Then, hydrogen chloride is removed from the reaction product by distillation or gas-liquid phase separation. After that, the target product, 1,1,1-trifluoroacetone of high purity, is obtained by rectification.

The following nonlimitative examples are illustrative of the present invention.

EXAMPLE 1

Synthesis of 1,1,1-trifluoroacetone

At first, a stainless steel tubular reactor was charged with 240 g of a catalyst (0.5% Pd on activated carbon) made by NE CHEMCAT CORPORATION. This catalyst contained 0.005 g of palladium (calculated as metallic form) per 1 g of activated carbon and was one prepared by a sufficient drying treatment. Then, the reactor was heated to 150° C. by a heat medium, while hydrogen gas was allowed to flow through the reactor at a rate of 0.8 liter/min by upflow from the bottom of the reactor towards the top of the reactor. Then, 240 g (1.44 mol) of 3-chloro-1,1,1,3-tetrafluoroacetone (gas chromatographic purity: 99.0%) were introduced into a vaporizer at a rate of 2 g/min, thereby vaporizing the same. The resulting vapor was mixed with hydrogen gas, and the mixture was introduced into the reactor after the reactor's inside temperature became stable. Then, the reaction was conducted for 2 hr to complete the introduction of the total of the mixture. After this completion, nitrogen gas in place of hydrogen gas was allowed to flow therethrough for 1 hr at the same rate. During the reaction, liquid and gas flowing out of the reactor were introduced into 1,015 g of water cooled at 0° C., thereby collecting them. The collected product in an amount of 1,152 g was found by Karl Fischer's method to contain 86.9 wt % (1,001 g) of water. Furthermore, the chemical composition (151 g) except water was analyzed by gas chromatography. With this, it was found to contain 98.4% (1.33 moles) of 1,1,1-trifluoroacetone (yield: 92%). The percentage is areal percentage in chromatogram.

EXAMPLE 2

Synthesis of 1,1,1-trifluoroacetone

At first, a stainless steel tubular reactor was charged with 240 g of the same catalyst as that of Example 1. Then, the reactor was heated to 150° C. by a heat medium, while hydrogen gas was allowed to flow through the reactor at a rate of 0.8 liter/min by upflow. Then, 240 g of a mixed liquid containing as main components 3-chloro-1,1,1,3-tetrafluoroacetone, 3-chloro-1,1,1-trifluoroacetone and 3,3-dichloro-1,1,1-trifluoroacetone were introduced into a vaporizer at a rate of 2 g/min, thereby vaporizing the same. In fact, the mixed liquid was found by gas chromatography to contain 48.2% of 3-chloro-1,1,1,3-tetrafluoroacetone, 24.5% of 3-chloro-1,1,1-trifluoroacetone and 25.6% of 3,3-dichloro-1,1,1-trifluoroacetone. The resulting vapor was mixed with hydrogen gas, and the mixture was introduced into the reactor after the reactor's inside temperature became stable. Then, the reaction was conducted for 2 hr to complete the introduction of the total of the mixture. After this completion, nitrogen gas in place of hydrogen gas was allowed to flow therethrough for 1 hr at the same rate. During the reaction, liquid and gas flowing out of the reactor were introduced into 1,020 g of water cooled at 0° C., thereby collecting them. The collected product in an amount of 1,157 g was found by Karl Fischer's method to contain 87.2 wt % (1,010 g) of water. Furthermore, the chemical composition (147 g) except water was analyzed by gas chromatography. With this, it was found to contain 97.2% (areal percentage) of 1,1,1-trifluoroacetone.

EXAMPLE 3

Synthesis of 1,1,1-trifluoroacetone

At first, a stainless steel tubular reactor was charged with 240 g of a catalyst (0.5% Pd and 0.1% Ag on activated carbon) made by NE CHEMCAT CORPORATION. This catalyst contained 0.005 g of palladium (calculated as metallic form) and 0.001 g of silver (calculated as metallic form) per 1 g of activated carbon and was one prepared by a sufficient drying treatment. Then, the reactor was heated to 150° C. by a heat medium, while hydrogen gas was allowed to flow through the reactor at a rate of 0.8 liter/min by upflow. Then, 240 g (1.43 mol) of 3-chloro-1,1,1,3-tetrafluoroacetone (gas chromatographic purity: 98.2%) were introduced into a vaporizer at a rate of 2 g/min, thereby vaporizing the same. The resulting vapor was mixed with hydrogen gas, and the mixture was introduced into the reactor after the reactor's inside temperature became stable. Then, the reaction was conducted for 2 hr to complete the introduction of the total of the mixture. After this completion, nitrogen gas in place of hydrogen gas was allowed to flow therethrough for 1 hr at the same rate. During the reaction, liquid and gas flowing out of the reactor were introduced into 1,010 g of water cooled at 0° C., thereby collecting them. The collected product in an amount of 1,145 g was found by Karl Fischer's method to contain 87.4 wt % (1,001 g) of water. Furthermore, the chemical composition (144 g) except water was analyzed by gas chromatography. With this, it was found to contain 97.8% (1.26 moles) of 1,1,1-trifluoroacetone (yield: 88%).

EXAMPLE 4

Synthesis of 1,1,1-trifluoroacetone

At first, 240 g (1.43 moles) of 3-chloro-1,1,1,3-tetrafluoroacetone (gas chromatographic purity: 98.2%) were mixed with 240 g of water, thereby preparing 480 g of an aqueous solution of 3-chloro-1,1,1,3-tetrafluoroacetone. Separately, a stainless steel tubular reactor was charged with 240 g of the same catalyst as that of Example 1. Then, the reactor was heated to 150° C. by a heat medium, while hydrogen gas was allowed to flow through the reactor at a rate of 0.8 liter/min by upflow. Then, 480 g of the above aqueous solution were introduced into a vaporizer at a rate of 2 g/min, thereby vaporizing the same. The resulting vapor was mixed with hydrogen gas, and the mixture was introduced into the reactor after the reactor's inside temperature became stable. Then, the reaction was conducted for 4 hr to complete the introduction of the total of the mixture. After this completion, nitrogen gas in place of hydrogen gas was allowed to flow therethrough for 1 hr at the same rate. During the reaction, liquid and gas flowing out of the reactor were introduced into 1,012 g of water cooled at 0° C., thereby collecting them. The collected product in an amount of 1,395 g was found by Karl Fischer's method to contain 89.2 wt % (1,245 g) of water. Furthermore, the chemical composition (150 g) except water was analyzed by gas chromatography. With this, it was found to contain 98.0% (1.31 moles) of 1,1,1-trifluoroacetone (yield: 92%).

The entire disclosure of Japanese Patent Application No. 2001-355054 filed on Nov. 20, 2001, including specification, claims and summary, is incorporated herein by reference in its entirety.

What is claimed is:

1. A process for producing 1,1,1-trifluoroacetone, comprising:

conducting in a gas phase a hydrogenolysis of a tetrafluoroacetone, represented by formula [1] with hydrogen gas in the presence of a catalyst comprising a transition metal,

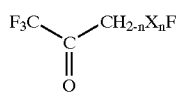

[1]

where X represents a chlorine, bromine or iodine, and n represents an integer from 0 to 2.

2. A process according to claim 1, wherein said transition metal is selected from the group consisting of ruthenium, palladium, platinum, iridium, rhodium, nickel, and a mixture of these.

3. A process according to claim 2, wherein said transition metal is selected from the group consisting of palladium, platinum, and a mixture of these.

4. A process according to claim 1, wherein said catalyst further comprises a support supporting thereon said transition metal.

5. A process according to claim 4, wherein said support is selected from the group consisting of activated carbon, alumina, silica-alumina, and silica.

6. A process according to claim 5, wherein said support is activated carbon and wherein said transition metal is palladium or platinum.

7. A process according to claim 4, wherein said transition metal is in an amount of 0.1–10 g per 100 g of said support.

8. A process according to claim 1, wherein said hydrogenolysis is conducted in the presence of water.

9. A process according to claim 1, wherein a hydrate of said tetrafluoroacetone is used as a raw material for conducting said hydrogenolysis.

10. A process according to claim 1, wherein an aqueous solution of a hydrate of said tetrafluoroacetone is used as a raw material for conducting said hydrogenolysis.

11. A process according to claim 1, wherein an aqueous solution of said tetrafluoroacetone is used as a raw material for conducting said hydrogenolysis.

12. A process according to claim 1, wherein said hydrogenolysis is conducted at a temperature of 50–300° C.

13. A process according to claim 1, wherein said hydrogen gas is in an amount of 1.5–50 moles per mole of said tetrafluoroacetone.

14. A process for producing 1,1,1-trifluoroacetone, comprising:

conducting in a gas phase a hydrogenolysis of a mixture of a tetrafluoroacetoner represented by formula [1], and a halogenated trifluoroacetone, represented by formula [2], with hydrogen gas in the presence of a catalyst comprising a transition metal,

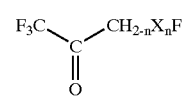

[1]

where X represents a chlorine, bromine or iodine, and n represents an integer from 0 to 2, and

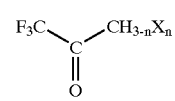

[2]

where X represents a chlorine, bromine or iodine, and n represents an integer from 1 to 3.

* * * * *